(12) United States Patent
Liu et al.

(10) Patent No.: US 12,097,036 B2
(45) Date of Patent: Sep. 24, 2024

(54) METHOD FOR CONSTRUCTING INTRACARDIAC ABNORMAL ACTIVATION POINT LOCATION MODEL BASED ON CNN AND LSTM

(71) Applicant: ZHEJIANG UNIVERSITY, Hangzhou (CN)

(72) Inventors: Huafeng Liu, Hangzhou (CN); Qiupeng Feng, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 465 days.

(21) Appl. No.: 17/618,495

(22) PCT Filed: Dec. 20, 2019

(86) PCT No.: PCT/CN2019/126940
§ 371 (c)(1),
(2) Date: Dec. 12, 2021

(87) PCT Pub. No.: WO2021/022763
PCT Pub. Date: Feb. 11, 2021

(65) Prior Publication Data
US 2022/0233129 A1    Jul. 28, 2022

(30) Foreign Application Priority Data

Aug. 6, 2019   (CN) .......................... 201910721820.2

(51) Int. Cl.
*A61B 5/363*    (2021.01)
*A61B 5/333*    (2021.01)
(Continued)

(52) U.S. Cl.
CPC .............. *A61B 5/363* (2021.01); *A61B 5/333* (2021.01); *A61B 5/364* (2021.01); *A61B 5/366* (2021.01);
(Continued)

(58) Field of Classification Search
CPC ......... A61B 5/333; A61B 5/363; A61B 5/364; A61B 5/366; A61B 5/367; A61B 5/7267;
(Continued)

(56) References Cited

U.S. PATENT DOCUMENTS

2017/0032221 A1    2/2017   Wu et al.
2019/0090774 A1*   3/2019   Yang ...................... A61B 5/303

FOREIGN PATENT DOCUMENTS

| CN | 107007279 | 8/2017 |
|----|-----------|--------|
| CN | 109567793 | 4/2019 |
| CN | 109645980 | 4/2019 |

* cited by examiner

*Primary Examiner* — George Manuel
(74) *Attorney, Agent, or Firm* — Jiwen Chen; Joywin IP Law PLLC

(57) ABSTRACT

The present invention discloses a method for constructing an intracardiac abnormal activation point location model based on CNN and LSTM. The model can well locate specific locations of abnormal activation points of VT and obtain three-dimensional coordinates of the locations, while obtaining 12-lead body surface potential data of a patient. The method introduces an idea of deep learning into locating of the abnormal activation points of ventricular tachycardia, uses collected QRS data as an input in a training phase, as well as three-dimensional coordinates of the QRS data corresponding to mapping points as a label to train a CNN-LSTM network, utilizes Conv1D to extract features from the input data, employs LSTM for feature fusion in a time domain, and exploits fully connected layers for regression prediction of the three-dimensional coordinates to finally construct the CNN-LSTM network. The network model of the present invention achieves prediction of the locations of the abnormal activation points of VT from a perspective of data drive, thus effectively solving a problem that clinical catheter ablation time consuming and laborious.

8 Claims, 2 Drawing Sheets

(51) Int. Cl.
    *A61B 5/364*     (2021.01)
    *A61B 5/366*     (2021.01)
    *G06N 3/044*     (2023.01)
    *G06N 3/045*     (2023.01)
    *G06N 3/063*     (2023.01)
    *G06N 3/08*     (2023.01)

(52) U.S. Cl.
    CPC .............. *G06N 3/044* (2023.01); *G06N 3/045* (2023.01); *G06N 3/063* (2013.01); *G06N 3/08* (2013.01)

(58) Field of Classification Search
    CPC ........ G06N 3/044; G06N 3/045; G06N 3/063; G06N 3/08
    See application file for complete search history.

Feature extraction     Feature fusion     Regression Prediction

METHOD FOR CONSTRUCTING INTRACARDIAC ABNORMAL ACTIVATION POINT LOCATION MODEL BASED ON CNN AND LSTM

This is a U.S. national stage application of PCT Application No. PCT/CN2019/126940 under 35 U.S.C. 371, filed Dec. 20, 2019 in Chinese, claiming priority of Chinese Application No. 201910721820.2, filed Aug. 6, 2019, all of which are hereby incorporated by reference.

FIELD OF TECHNOLOGY

The present invention belongs to the technical field of cardiac electrophysiology analysis and specifically relates to a method for constructing an intracardiac abnormal activation point location model based on CNN (convolutional neural network) and LSTM (long short-term memory).

BACKGROUND TECHNOLOGY

Machine learning is a product of development of artificial intelligence. To make a machine intelligent, it must be endowed with the ability to learn; for a machine, real life is a huge data set filled with all kinds of data. All machine learning has to do is to reveal true meanings hidden in the data and be able to make accurate predictions. A mainstream machine learning method mainly relies on statistics, using massive amounts of data to extract valuable information therefrom for learning, and establishing a model for judgment and prediction. Recently, with the improvement of computer performance, a deep learning method represented by a neural network can use a gradient descent method to iteratively update network parameters through the training of a large amount of data to improve model performances. For a problem of heart positioning, we use a deep learning method to allow the network to automatically learn hidden information in electrocardiograms (ECGs) to locate abnormal points of the heart. A convolutional neural network and a recurrent neural network are representative algorithms of deep learning, wherein the convolutional neural network has good representation and feature extraction capabilities, while the recurrent neural network is good at processing time series data, which combines an input of each current moment with an output of a previous moment to learn a feature of overall time series information.

The heart is an important organ of a human body. Due to rhythmic excitement of sinoatrial nodes, the normal heart will cause regular contraction and relaxation of the heart muscle, which will spread through a special conduction system. The conduction system of the heart includes sinoatrial node, internodal bundle, atrioventricular node, His bundle, bundle branch, and Purkinje fiber, which are composed of specially differentiated cardiomyocytes (including sinoatrial node cells and Purkinje cells) and produce and maintain the normal rhythm of the heart to ensure the coordination of the contraction and relaxation of the atria and ventricles. If a certain part of the conduction system is abnormal, it will lead to corresponding abnormality of electrocardiogram signals; ventricular tachycardia (VT) is a tachyarrhythmia that occurs in the bundle branch, myocardial conduction fiber, and ventricular muscle below the bifurcation of the His bundle, and is also a very serious arrhythmia. The cause of most VT patients is the presence of "small circuits" in the ventricles, which generally exist in myocardial ischemic lesions, and the exit point in the lesions will depolarize the surrounding ventricle portion; the effective way to treat VT is to use catheter ablation to destroy this exit to cut off the "small circuits", and because of the existence of this exit, the "small circuits" will affect electrocardiogram signal values measured on the body surface, so the electrocardiogram contains signals of abnormal heart points.

In the process of heart excitement, cardiomyocytes will generate action potentials to generate electrical signals. The electrical signals generated can be transmitted to the body surface through the conductive tissues or body fluids around the heart, and thus are received by external electrodes on the body surface to become an electrocardiogram. Therefore, the electrocardiogram records the visual time series of the bioelectric activity of the human heart, which reliably reflects the comprehensive performance of the human heart; abnormalities in the transmission of the cardiac potential will also be mapped in the electrocardiogram in some forms, becoming a main basis for the diagnosis of contemporary doctors.

Although the current clinical diagnosis of ventricular tachycardia mainly depends on a 12-lead electrocardiogram, such a method can only make a preliminary diagnosis of VT to determine whether a patient suffers from diseases such as ventricular tachycardia, and cannot provide more detailed information such as specific occurrence locations of tachycardia. On the other hand, in the process of clinical treatment of VT, we need to use catheter ablation to perform localized treatment on focus points. At present, surgeons need to directly measure an electrophysiological activity at a target position of the heart by means of an invasive means to locate abnormal activation points of VT, thus facilitating implementation of a following fixed-point ablation surgery. However, an invasive pacing mapping method is inefficient, time-consuming, laborious, and certainly risky.

Therefore, how to locate abnormal activation points of VT in vitro based on the existing diagnosis and treatment methods has become a very significant research question. With the development of modern science and technology, use of computer-assisted means to locate abnormal activation points of VT becomes possible.

SUMMARY OF THE INVENTION

In view of the foregoing, the present invention is to provide a method for constructing an intracardiac abnormal activation point location model based on CNN (Convolutional Neural Network) and LSTM (Long Short Term Memory). The model can accurately locate specific locations of abnormal activation points of VT and obtain three-dimensional coordinates of the locations, while obtaining 12-lead body surface potential data of a patient.

A method for constructing an intracardiac abnormal activation point location model based on CNN and LSTM comprises following steps:

(1) using a pacing and mapping tool to collect 12-lead body surface ECG data of different mapping points on different VT patients and recording three-dimensional coordinates of the mapping points corresponding to each set of the 12-lead body surface ECG data;

(2) preprocessing the 12-lead body surface ECG data and marking a QRS interval;

(3) for any set of the 12-lead body surface ECG data, screening and splicing QRS complexes therein to obtain a plurality of feature samples; and (4) constructing a network model based on CNN and LSTM and using the feature samples and the three-dimensional coordinates of the mapping points corresponding to the feature samples as truth-value labels of a model input and a model output, respectively, so as to train the network model to obtain a locating model for determining locations of intracardiac abnormal activation points.

Further, a specific implementing process of the step (1) is as follows: firstly attaching medical 12-lead lead body surface electrode patches to a patient to collect a 12-lead ECG signal of the patient; then employing a CARTO3 system to select an appropriate left ventricular membrane position for three-dimensional electroanatomical mapping, and recording the 12-lead body surface ECG data and the three-dimensional coordinates of each mapping point.

Further, a specific implementing process of the step (2) is as follows: firstly denoising an ECG signal of each channel in the 12-lead body surface ECG data by filtering, then smoothing the denoised ECG signal in a polynomial fitting manner, and finally marking the QRS interval in each cardiac cycle of the smoothed ECG signal.

Further, a specific implementing process of the step (3) is as follows: firstly artificially selecting appropriate QRS complexes from each set of the 12-lead body surface ECG data by professionals, expanding the QRS complexes in a same cardiac cycle into 12 sets of QRS data according to lead positions, and successively splicing the 12 sets of QRS data as a feature sample.

Preferably, all the feature samples in the step (4) are divided into a training set, a verification set and a test set, wherein the feature samples of the training set are used for training the network model, the feature samples of the verification set are used for fine-tuning the model obtained from training to determine the final location model, and the feature samples of the test set are used for performing test validation on the location model.

Preferably, gaussian noises are added to the feature samples of the training set as an input to train the network model, such that the model has anti-noise capacity, for the actual input data are collected real ECG signals and have noises, so it is necessary to perform denoising during the training process thereof.

Further, a specific implementing process of training the network model the step (4) is as follows: firstly inputting the feature samples into the network model one by one, calculating a loss function L between each output result of the network model and a corresponding truth-value label, continuously optimizing parameters in the network model using a back propagation method with the goal of minimizing the loss function L, and finally completing training to obtain the location model used to determine the locating model for determining the locations of the intracardiac abnormal activation points.

Further, the network model is formed by, from the input to the output, sequentially connecting two one-dimensional convolutional neural network layers A1~A2, a maximum pooling layer M1, two one-dimensional convolutional neural network layers A3~A4, a maximum pooling layer M2, three one-dimensional convolutional neural network layers A5~A7, two LSTM layers L1~L2, a global average pooling layer P, a discarding layer D, and four fully connected layers H1~H4, and an output of each one-dimensional convolutional neural network layer is subjected to batch normalization and ReLu function processing in turn, wherein both the one-dimensional convolutional neural network layers A1 and A2 contain 12 one-dimensional convolution kernels each with a size of 3×12 and a step length of 1, and an output length and an input length remain unchanged; the maximum pooling layer M1 is output after an input length thereof is reduced by half; both one-dimensional convolutional neural network layers A3 and A4 contain 24 one-dimensional convolution kernels each with a size of 3×12 and a step length of 1, and an output length and an input length thereof remain unchanged; the maximum pooling layer M2 is output after an input length thereof is reduced by half; the one-dimensional convolutional neural network layers A5~A7 all contain 48 one-dimensional convolution kernels each with a size of 3×12 and a step length of 1, and an output length and an input length thereof remain unchanged; the number of hidden layer neurons in the LSTM layer L1 is 128, and outputs of all time nodes thereof are retained; the number of hidden layer neurons in the LSTM layer L2 is 48, and outputs of all time nodes thereof is retained; the global average pooling layer P compresses output features of the LSTM layer L2 to 48 channel descriptors; the discarding layer D randomly selects 50% of network weight parameters to reset to 0; the number of neurons in the fully connected layer H1 is 48; the number of neurons in the fully connected layer H2 is 24; the number of neurons in the fully connected layer H3 is 12; and the number of neurons in the fully connected layer H4 is 3.

The method of the present invention introduces an idea of deep learning into locating of the abnormal activation points of ventricular tachycardia, uses collected QRS data as an input in a training phase, as well as three-dimensional coordinates of the QRS data corresponding to mapping points as a label to train a CNN-LSTM network, utilizes Conv1D to extract features from the input data, employs LSTM for feature fusion in a time domain, and exploits fully connected layers for regression prediction of the three-dimensional coordinates to finally construct the CNN-LSTM network. The network model of the present invention achieves prediction of the locations of the abnormal activation points of VT from a perspective of data drive, thus effectively solving a problem that clinical catheter ablation is time consuming and laborious.

DESCRIPTION OF THE EMBODIMENTS

To more explicitly describe the present invention, the technical solution of the present invention will be described in detail with reference to the accompanying figures and embodiments hereinafter.

Figure 2:
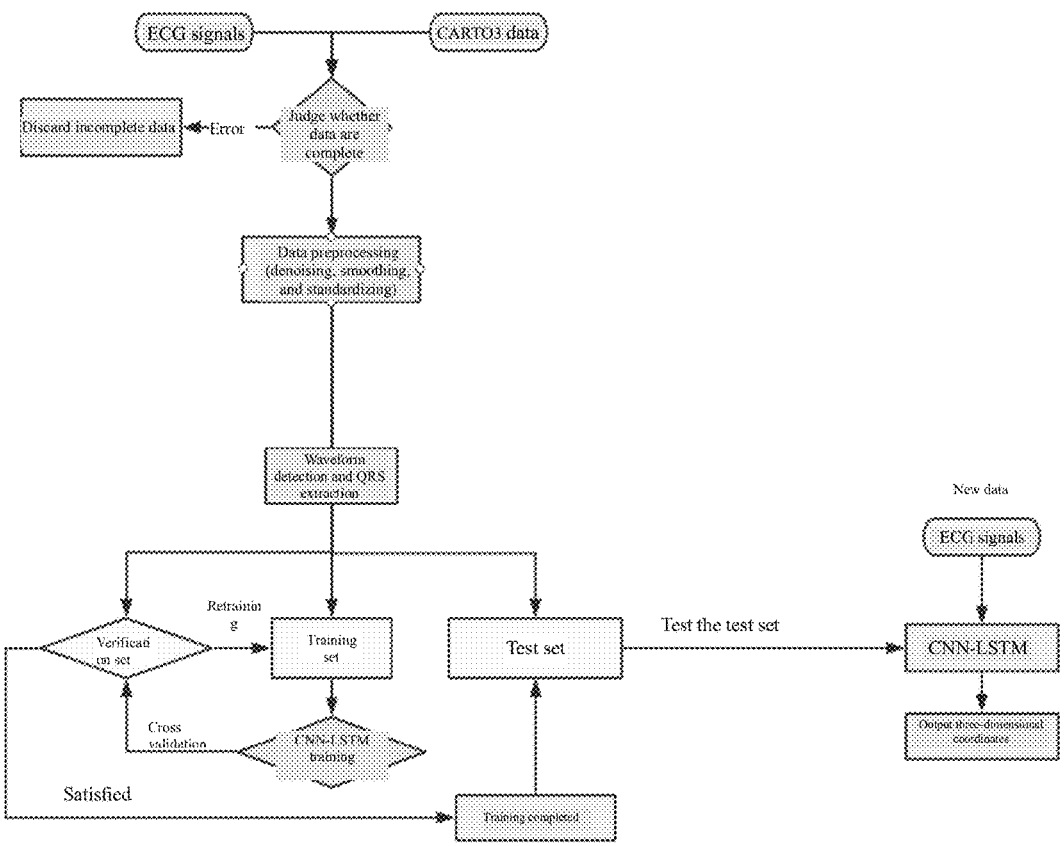
FIG. 2 is a whole process schematic diagram of a method of the present invention.

As shown in FIG. 2, specific implementing steps of a method for constructing an intracardiac abnormal activation point location model based on CNN and LSTM in the present application are as follows:

S1. Collecting 12-lead body surface potential data of a VT patient and recording three-dimensional coordinates of corresponding mapping points.

Firstly, common medical 12-lead body surface electrode patches were attached to a patient to collect 12-lead body surface potential data of the patient; then, a CARTO3 system was employed to select an appropriate left ventricular membrane position for three-dimensional electroanatomical mapping, and 12-lead ECG signals at corresponding locations and the three-dimensional coordinates of the mapping points were recorded. The data of the present invention were collected from 39 VT patients during catheter ablation. In this example, a total of 1012 independent points and 16848 valid QRS waveform data were collected from the left ventricular membrane of the patient. Each data were composed of 100 values of 12 leads.

S2. Pretreating the collected 12-lead body surface potential data.

Firstly, a potential signal of each channel was denoised by filtering, then the denoised potential signal of each channel in a polynomial fitting manner was smoothed, and finally the QRS interval in each cardiac cycle was marked. The above steps were both completed on public software ECGViewer.

S3. Selecting appropriate QRS complexes and generate input data.

In order to avoid the selected complexes from being ectopic or non-captured heart beats, the appropriate QRS complexes were selected from the data by professionals, the stacked 12-lead QRS complexes were expanded according to the lead position, and the complexes were spliced according to positions (I II III aVR aVL aVF V1 V2 V3 V4 V5 V6) of body surface electrodes; then sampling was performed on a time axis with the QRS data size of each lead of 100*1 to finally obtain the input data for modeling with a size of 1200*1. Since each ECG signal can collect multiple QRSs, a total of 16848 groups of data sets were collected. Each group of data has a corresponding x-y-z three-dimensional coordinate as a label. If two QRSs were collected from one ECG signal, the labels for both were the same.

S4. Dividing the data sets.

The data sets and corresponding three-dimensional coordinates were divided into a training set (22 patients, 10299 groups of data), a verification set (5 patients, 3017 groups of data), and a test set (12 patients, 3539 groups of data).

S5. In the training process, Conv1D (one-dimensional convolutional neural network layer) was used to extract features of the ECG signals. Since an ECG signal was a fixed-length one-dimensional time series, the present invention employed the one-dimensional convolutional neural network layer, which had been well applied to processing of time series such as a natural language. This part included a total of six one-dimensional convolutional layers and two maximum pooling layers, and each Conv1D defines a filter with a length of 3.

Figure 3:
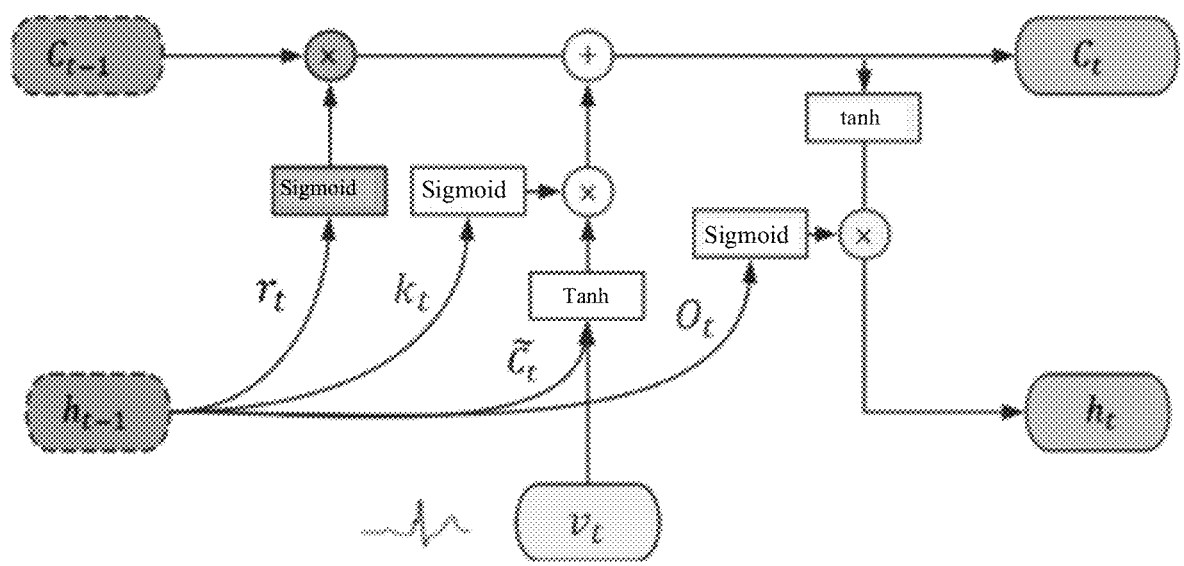
FIG. 3 is a structure diagram of an LSTM network.

S6. In the present invention, the two-layer LSTM was used as a time series fusion network to train and process high-dimensional features in the time domain. The LSTM was an improved model based on RNN and can learn information with long-term dependence. Hidden layers of the LSTM were also called LSTM units. The number of the LSTM units was determined by an input length in the time direction. The dimension of the LSTM units, i.e., the number of neurons in each unit, determines an output size. At each step t, the LSTM units receive an input $v_t$, a previous output $h_{t-1}$, and a previous unit state $C_{t-1}$, and then calculate an output $h_t$ and a unit state $C_t$, as shown in FIG. 3. Due to a gating structure, the LSTM can handle long-term dependence by allowing useful information to be transmitted through the network. There were three gates in the LSTM units, including an input gate, a forgetting gate, and an output gate. A forgetting gate layer determines through parameters the information that will be discarded from the previous unit state $C_{t-1}$, wherein 0 represents "discard the information completely" and 1 represents "retain all information"; then, the input gate determines which new information of the input $v_t$ needs to be stored in a current time step; and finally, the output gate generates a new cell state $C_t$.

S7. The present invention utilized a three-layer fully connected neural network layer to predict the three-dimensional coordinates of the abnormal activation points of VT. Through a three-layer fully connected convolution operation, we can use the previously extracted features to predict the three-dimensional coordinates of the abnormal activation points of VT.

Figure 1:
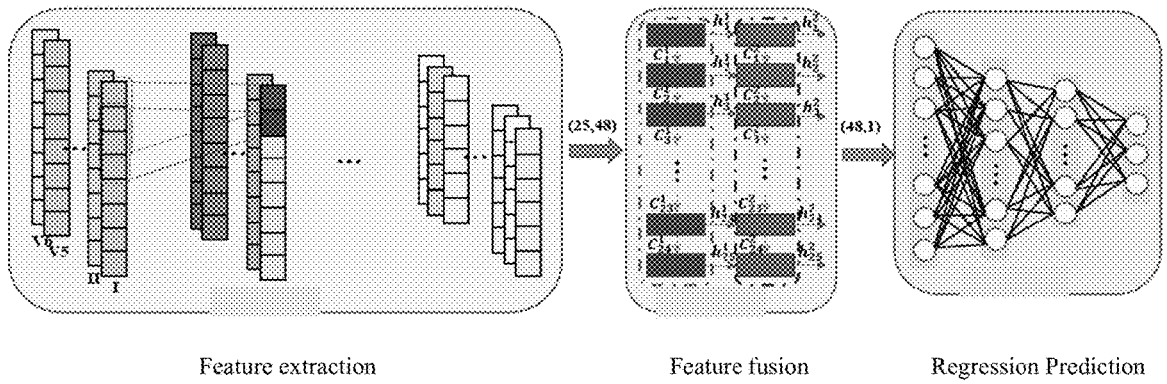
FIG. 1 is an overall framework schematic diagram of a network model of the present invention.

S8. As shown in FIG. 1, we firstly input a waveform $v_t$ of an ECG in an input data set in the training set into a six-layer Conv1D for feature extraction, then input extracted features into a two-layer LSTM network, then performed fusion processing on an entire time domain, output high-dimensional features to the fully connected layer for regression prediction to obtain a predicted coordinate $\bar{S}$ of the abnormal activation points of VT, then calculated a difference between the predicted coordinate with a true value label (a three-dimensional coordinate) S for improvement with a calculation formula as follows:

$$\min\|\tilde{S}(x, y, z) - S(x, y, z)\|^2$$

to finally obtain our locating model of the abnormal activation points of VT, and fine tune the model with data in the verification set to obtain an optimal model.

S9. The test set was input into the locating model of the intracardiac abnormal activation point to obtain a test result, the test result was compared with a real value, and a real location and a prediction location were displayed in the three-dimensional coordinate system. The specific operation process was as follows: inputting the waveform $v_t$ of the ECG in the input data set in the test set into a trained CNN-LSTM model to obtain a final coordinate prediction result (x-y-z) in an output layer of the model, and displaying the prediction result and the true value in the three-dimensional coordinate system for visual observation.

S10. In the specific implementation process, the entire algorithm was tested in Ubuntu 14.04 LTS (64-bit) system, where a CPU was Core i7-7800X (3.5 GHz), a host memory was 32 GB RAM, and a graphics card model was NVIDIA GTX1080Ti (12 GB memory). In programming, a Keras platform using Tensorflow was used to build a neural network. The platform was based on the Python language and can be used in combination in multiple program development environments.

The foregoing description of the examples is intended to facilitate the understanding and application of the present invention by those of ordinary skill in the art. Those skilled in the art can obviously easily make various amendments to the above examples and apply the general principles described herein to other examples without any ingenuity. Therefore, the present invention is not limited to the above examples, and any improvement or amendment of the present invention made by those skilled in the art according to the disclosure of the present invention shall fall within the scope of protection of the invention.

What is claimed is:

1. A method for constructing an intracardiac abnormal activation point location model based on convolutional neural network (CNN) and long short-term memory (LSTM), comprising following steps:
   (1) using a pacing and mapping tool to collect 12-lead body surface electrocardiogram (ECG) data of different mapping points on different ventricular tachycardia (VT) patients and recording three-dimensional coordinates of the mapping points corresponding to each set of the 12-lead body surface ECG data;

(2) preprocessing the 12-lead body surface ECG data and marking a QRS interval;

(3) for any set of the 12-lead body surface ECG data, screening and splicing QRS complexes therein to obtain a plurality of feature samples; and (4) constructing a network model based on CNN and LSTM and using the feature samples and the three-dimensional coordinates of the mapping points corresponding to the feature samples as truth-value labels of a model input and a model output, respectively, so as to train the network model to obtain a locating model for determining locations of intracardiac abnormal activation points.

2. The method for constructing an intracardiac abnormal activation point location model according to claim 1, wherein a specific implementing process of the step (1) is as follows: firstly attaching medical 12-lead lead body surface electrode patches to a patient to collect a 12-lead ECG signal of the patient; then employing a CARTO3 system to select an appropriate left ventricular membrane position for three-dimensional electroanatomical mapping, and recording the 12-lead body surface ECG data and the three-dimensional coordinates of each mapping point.

3. The method for constructing an intracardiac abnormal activation point location model according to claim 1, wherein a specific implementing process of the step (2) is as follows: firstly denoising an ECG signal of each channel in the 12-lead body surface ECG data by filtering, then smoothing the denoised ECG signal in a polynomial fitting manner, and finally marking the QRS interval in each cardiac cycle of the smoothed ECG signal.

4. The method for constructing an intracardiac abnormal activation point location model according to claim 1, wherein a specific implementing process of the step (3) is as follows: firstly artificially selecting appropriate QRS complexes from each set of the 12-lead body surface ECG data by professionals, expanding the QRS complexes in a same cardiac cycle into 12 sets of QRS data according to lead positions, and successively splicing the 12 sets of QRS data as a feature sample.

5. The method for constructing an intracardiac abnormal activation point location model according to claim 1, wherein all the feature samples in the step (4) are divided into a training set, a verification set and a test set, wherein the feature samples of the training set are used for training the network model, the feature samples of the verification set are used for fine-tuning the model obtained from training to determine the final location model, and the feature samples of the test set are used for performing test validation on the location model.

6. The method for constructing an intracardiac abnormal activation point location model according to claim 5, wherein gaussian noises are added to the feature samples of the training set as an input to train the network model.

7. The method for constructing an intracardiac abnormal activation point location model according to claim 1, wherein a specific implementing process of training the network model the step (4) is as follows: firstly inputting the feature samples into the network model one by one, calculating a loss function L between each output result of the network model and a corresponding truth-value label, continuously optimizing parameters in the network model using a back propagation method with the goal of minimizing the loss function L, and finally completing training to obtain the location model used to determine the locating model for determining the locations of the intracardiac abnormal activation points.

8. The method for constructing an intracardiac abnormal activation point location model according to claim 1, wherein the network model is formed by, from the input to the output, sequentially connecting two one-dimensional convolutional neural network layers A1~A2, a maximum pooling layer M1, two one-dimensional convolutional neural network layers A3~A4, a maximum pooling layer M2, three one-dimensional convolutional neural network layers A5~A7, two LSTM layers L1~L2, a global average pooling layer P, a discarding layer D, and four fully connected layers H1~H4, and an output of each one-dimensional convolutional neural network layer is subjected to batch normalization and ReLu function processing in turn, wherein both the one-dimensional convolutional neural network layers A1 and A2 contain 12 one-dimensional convolution kernels each with a size of 3×12 and a step length of 1, and an output length and an input length thereof remain unchanged; the maximum pooling layer M1 is output after an input length thereof is reduced by half; both one-dimensional convolutional neural network layers A3 and A4 contain 24 one-dimensional convolution kernels each with a size of 3×12 and a step length of 1, and an output length and an input length thereof remain unchanged; the maximum pooling layer M2 is output after an input length thereof is reduced by half; the one-dimensional convolutional neural network layers A5~A7 all contain 48 one-dimensional convolution kernels each with a size of 3×12 and a step length of 1, and an output length and an input length thereof remain unchanged; the number of hidden layer neurons in the LSTM layer L1 is 128, and outputs of all time nodes thereof are retained; the number of hidden layer neurons in the LSTM layer L2 is 48, and outputs of all time nodes thereof is retained; the global average pooling layer P compresses output features of the LSTM layer L2 to 48 channel descriptors; the discarding layer D randomly selects 50% of network weight parameters to reset to 0; the number of neurons in the fully connected layer H1 is 48; the number of neurons in the fully connected layer H2 is 24; the number of neurons in the fully connected layer H3 is 12; and the number of neurons in the fully connected layer H4 is 3.

\* \* \* \* \*